United States Patent [19]
Walker et al.

[11] Patent Number: 5,570,697
[45] Date of Patent: Nov. 5, 1996

[54] SENSOR FOR ANALYZING MOLECULAR SPECIES

[75] Inventors: Stephen D. Walker; Jack L. Jewell; Greg R. Olbright; Stanley E. Swirhun, all of Boulder, Colo.

[73] Assignee: Vixel Corporation, Broomfield, Colo.

[21] Appl. No.: 275,456

[22] Filed: Jul. 15, 1994

[51] Int. Cl.$^6$ .............................. A62B 7/00; A61B 5/097; A61B 5/00
[52] U.S. Cl. ............................................ 128/719; 128/633
[58] Field of Search .................................. 128/718, 719, 128/633, 665, 667, 664; 250/343; 422/84

[56] References Cited

U.S. PATENT DOCUMENTS

| | | | |
|---|---|---|---|
| 4,522,204 | 6/1985 | Kurahashi et al. | 128/719 |
| 4,648,396 | 3/1987 | Raemer | 128/719 |
| 4,730,112 | 3/1988 | Wong . | |
| 4,807,637 | 2/1989 | Bjorkholm | 128/665 |
| 4,934,816 | 6/1990 | Silver et al. . | |
| 4,955,946 | 9/1990 | Mount et al. | 128/719 |
| 4,998,018 | 3/1991 | Kurahashi et al. | 128/719 |
| 5,092,342 | 3/1992 | Hattendorff et al. | 128/719 |
| 5,095,900 | 3/1992 | Fertig et al. | 128/719 |
| 5,130,544 | 7/1992 | Nilsson | 128/719 |
| 5,173,432 | 12/1992 | Lefkowitz et al. | 128/664 |
| 5,282,473 | 2/1994 | Braig et al. | 128/719 |
| 5,355,880 | 10/1994 | Thomas et al. | 128/665 |
| 5,382,163 | 1/1995 | Putnam | 128/665 |
| 5,423,320 | 6/1995 | Salzman et al. | 128/664 |

OTHER PUBLICATIONS

Periläinen, "Sensors for Oxygen Analysis: Paramagnetic, Electrochemical, Polarographic, and Zirconium Oxide Technologies," Biomedical Instrumentation & Technology, Nov./Dec. 1989, pp. 462–466.

Sodal, "The Medical Mass Spectrometer," Biomedical Instrumentation & Technology, Nov./Dec. 1989, pp. 469–476.

Westenskow & Coleman, "Raman Scattering for Respiratory Gas Monitoring in the Operating Room: Advantages, Specifications, and Future Advances," Biomedical Instrumentation & Technology, Nov./Dec. 1989, pp. 485–489.

Olbright, Bryan, Fu, Apte, Bloom & Lee, "Linewidth, tunability, and VHF–Millimeter Wave Frequency Synthesis of Vertical–Cavity GaAs Quantum–Well Surface–Emitting Laser Diode Arrays," IEEE Photonics Technology Letters, vol. 3, No. 9, Sep. 1991, pp. 779–781.

Goldstein, Adler–Golden, Lee & Bien, "Measurement of molecular concentrations and line parameters using line–locked second harmonic spectroscopy with an AlGaAs diode laser," Applied Optics, vol. 31, No. 18, Jun. 20, 1992, pp. 3409–3415.

Cooper & Martinelli, "Near–infrared diode lasers monitor molecular species," Laser Focus World, Nov. 1992, pp. 133–146.

Chernin, "New Generation of Multipass Systems," SPIE vol. 2112, pp. 99–108.

Barnikol, W. K. R., et al. "Microdetector for Rapid Changes of Oxygen Partial Pressure During the Respiratory Cycle in Small Laboratory Animals," [Rev.Sci.Instrum.] 59 (7), Jul. 1988, pp. 1204–1208.

Primary Examiner—Angela D. Sykes
Assistant Examiner—Stephen Huang
Attorney, Agent, or Firm—Irell & Manella LLP

[57] ABSTRACT

An on-airway breath-by-breath oxygen sensor is described which has the necessary low weight, fast response and high precision required for oxygen consumption measurement. A vertical-cavity surface-emitting laser (VCSEL) is continuously tuned to emit light at the resonance of oxygen, or more generally, the molecular species of interest. The light beam is directed through a sample containing the molecular species of interest onto a detector. The amount of light absorbed is approximately proportional to the concentration of the molecular species of interest in the sample.

60 Claims, 6 Drawing Sheets

SENSOR FOR ANALYZING MOLECULAR SPECIES

BACKGROUND OF THE INVENTION

1. Field of the Invention

The present invention relates to spectroscopic sensors and, more particularly, to a continuous breath by breath on-airway oxygen sensor.

2. Description of the Prior Art

Oxygen consumption measurement is necessary for accurate assessment of human cardiopulmonary function. Sensor requirements for measuring oxygen consumption are: (1) accuracy to measure the difference in oxygen concentration between inspired and expired gas thus giving oxygen consumption; (2) small size and light weight so the measurement can be made on the subject's airway with no discomfort: and (3) rapid response time to continuously analyze on a breath by breath basis. No prior art oxygen sensor meets all these requirements.

Oxygen sensor technologies were reviewed by P. S. Merilainen entitled "Sensors for Oxygen Analysis: Paramagnetic, Electrochemical, Polarographic, and Zirconium Oxide Technologies," *Biomedical Instrumentation & Technology*, 23, 6, 1989. Electrochemical cells and polarographic sensors both produce an electrical current proportional to the number of oxygen molecules which have diffused across a membrane. These sensors do not have the required last response time due to the slow diffusion process. Additionally, accuracy degrades towards the end of the cell's life, especially when exposed to high concentrations of oxygen. Accuracy is also affected by carbon dioxide, water vapor and anesthetic agents, all of which are contained in respiratory gas. Finally, these sensors are too large to attach to the subject's airway without causing discomfort. Paramagnetic sensors utilize the strong magnetic susceptibility of oxygen to determine concentration. A sample of respiratory gas and a reference gas are mixed within a homogeneous magnetic field. A pressure signal proportional to oxygen content difference between the two gases is generated when the direction of current to the coil of the magnet is reversed. This type of oxygen sensor cannot be attached to the subject's airway due to the large size and heavy mass of the required electromagnets.

Zirconium oxide sensors are constructed of a solid electrolyte tube made of zirconium oxide covered by porous Pt-electrodes on both sides. The side of the wall exposed to higher oxygen partial pressures becomes an anode, at which oxygen molecules are ionized and transported to a cathode through the wall. The voltage generated across a cell is proportional to the logarithm of the ratio between the sample gas and the reference gas. Zirconium oxide oxygen sensors cannot be mounted on the subject's airway because they require heating to 800 degrees Celsius and are a safety hazard.

Mass spectrometers spread ionized gas molecules into a spectrum according to their mass-to-charge ratios and cannot be attached to the subject's airway due to the large size and heavy mass of the required ionizing magnets and vacuum pumps, see I. E. Sodal, "The Medical Mass Spectrometer," *Biomedical Instrumentation & Technology*, Vol. 23, No. 6 (1989).

Raman scattering spectrometers measure re-emitted photons caused by the collision of a photon with an oxygen molecule. A photon from a high-power laser loses energy to the oxygen molecule and is re-emitted at a lower energy and frequency. The number of photons re-emitted at the oxygen Raman scattering wavelength is proportional to the number of oxygen molecules present. Raman scattering spectrometers cannot be attached to the subject's airway due to the large size and heavy mass of the required high-power laser, heat sink and thermoelectrically cooled detectors, see Westenskow et al., "Raman Scattering for Respiratory Gas Monitoring in the Operating Room: Advantages, Specifications, and Future Advances." *Biomedical Instrumentation & Technology*, Vol. 23, No. 6 (1989).

Frequency modulated spectroscopy as described by Bjorklund in U.S. Pat. No. 4,297,035 and dual frequency modulation spectroscopy as described by Gallagher in U.S. Pat. No. 4,765,736 are techniques for increased sensitivity to a molecular species of interest. These techniques have limitations because, until the present sensor, continuously tunable laser diodes have not been available for wavelengths shorter than 1200 nm, see Cooper et at., "Near-infrared diode lasers monitor molecular species," *Laser Focus World* (November 1992). Techniques to increase the path length through a small sample volume are also described, for example, in the publication by S. M. Chernin, entitled "A New Generation of Multipass Systems," SPIE Proc, Vol. 12112, pp. 99–108 (1994).

SUMMARY OF THE INVENTION

It is therefore an object of the present invention to provide a sensor for analyzing molecular species which will provide a laser that is tuned to emit light at the optical absorption resonance of a molecular species of interest. The laser beam is directed through a sample containing the molecular species of interest. The amount of light absorbed is proportional to the concentration of the molecular species of interest in the sample.

It is a further object to provide an oxygen sensor based on vertical-cavity surface-emitting lasers (VCSELs) which meet the accuracy, small size and rapid response requirements for oxygen consumption measurement.

It is yet another object to provide VCSELs or distributed feedback (DFB) lasers which may be continuously tuned to the oxygen resonances unlike conventional laser diodes.

It is yet another object to provide a sensor having an accuracy of ±0.5% which is adequate for determining oxygen consumption, metabolic monitoring and cardiac output.

It is yet another object to provide a sensor having a response time of less than 50 milliseconds enabling acquisition of real time oxygen waveforms up to 200 breaths per minute.

It is yet another object of the invention to provide a sensor which is small enough to be mounted on a trachea tube without causing discomfort to a subject or interfering with clinical personnel.

It is yet another object to provide a sensor which has no moving parts.

It is yet another object to provide a sensor which does not vibrate critical connections, of a subject, loose.

It is yet another object to provide a sensor in which critical components are not exposed to the humidity, blood, mucus, bacteria and vital agents present in a respiratory gas.

Finally, it is an object of the invention to provide a sensor which is inexpensive, small, lightweight and can be mounted on a subject's airway with no discomfort.

According to one broad aspect of the present invention, there is provided an oxygen sensor comprising: a first sample containing respiratory oxygen; and a sensor mechanism, the sensor mechanism utilizing an optical light source and weighing less than 50 grams and having a response time less than 15 seconds.

According to another broad aspect of the invention, there is provided a respiratory oxygen sensor comprising: a first laser diode emitting a first light beam having a first emission wavelength; a tuning means for tuning the first emission wavelength to an absorption resonance of oxygen; a first respiratory gas sample; a first directing means for irradiating the respiratory gas sample with the light beam; a first detector which receives at least a portion of the light beam and emits signals in response thereto; and means for interpreting the signals to measure the concentration of oxygen in the respiratory gas sample.

According to yet another broad aspect of the invention, there is provided an optical sensor comprising: at least a first light source, the first light source emitting a first light beam, the first light beam having a first wavelength of less than 1.2 micrometers which is continuously tunable and having a frequency linewidth of less than 3 gigahertz; at least a first power supply for applying power to the first light source; a first tuning means for tuning the first wavelength; a first sample containing a target species; a first directing means for irradiating the first sample with the first light beam; at least one detector which receives at least a portion of the first light beam and emits signals in response thereof; and a means for interpreting the signals.

Other objects and features of the present invention will be apparent from the following detailed description of the preferred embodiment.

BRIEF DESCRIPTION OF THE DRAWINGS

The invention will be further described in conjunction with the accompanying drawings, in which.

DETAILED DESCRIPTION OF THE PREFERRED EMBODIMENT

Figure 3B:
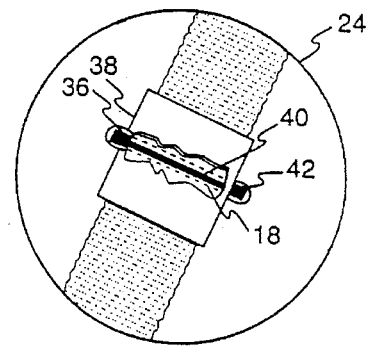
FIG. 3B is an enlarged view of an oxygen sensor constructed in accordance with a preferred embodiment of the invention.
Figure 3A:
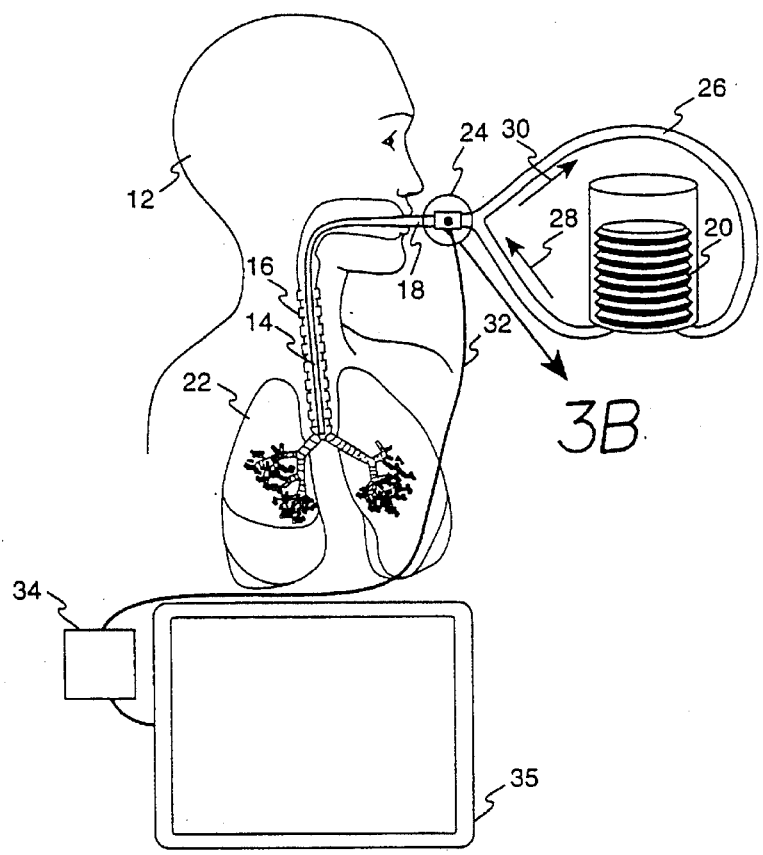
FIG. 3A illustrates respiratory oxygen consumption measurement utilizing a sensor constructed in accordance with a preferred embodiment of the invention.

With reference to the Figures, wherein like reference characters indicate like elements throughout the several views and, in particular, with reference to FIG. 3A, there is shown a preferred embodiment for the invention for analyzing the breath by breath respiratory oxygen concentrations, of a subject 12 undergoing a surgical procedure or critical care ventilation. Such subjects have a trachea tube 14 inserted in a trachea 16 to facilitate the flow of oxygen enriched air 18 between ventilator 20 and lungs 22. Oxygen sensor 24 is mounted on a distal end of trachea tube 14 which connects to breathing circuit 26. Both inspired 28 and expired 30 respiratory gas pass through sensor 24. Cable 32 connects sensor 24 with electronic control circuits 34 and display 35. An enlargement of sensor 24, which details laser diode 36 mounted on airway adapter 38, is illustrated in FIG. 3B. Laser beam 40 is directed through airway adapter 38 and respiratory gas 18 onto detector 42. The total pathlength of laser beam 40 is preferably 22 mm. Advantages of sensor 24 in this application are: (1) it is small enough to be mounted on trachea tube 14 without causing discomfort to subject 12 or interfering with clinical personnel; (2) it is lightweight, i.e., less than 50 grams; (3) it does not obstruct the subject's airway; (4) it is rugged; (5) it has no moving parts; (6) it does not vibrate critical connections loose; (7) it has the accuracy required to measure the difference between oxygen concentrations in inspired and expired gas, i.e., small changes which are less than 3 volume percent of the concentration; and (8) it has a rapid response time, i.e., less than 15 seconds, which enables the breath by breath measurement of inspired and expired respiratory gas.

Figure 4:
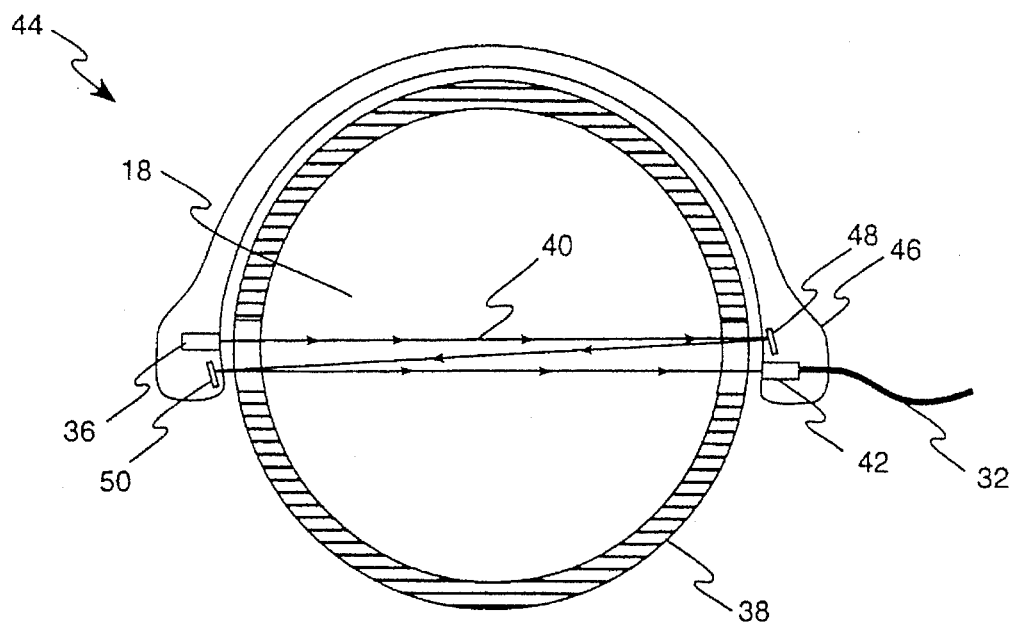
FIG. 4 is a cross-sectional view of an alternate embodiment of the invention which illustrates a multi-pass oxygen sensor.

Referring now to FIG. 4, there is shown multi-path sensor 44 housed in enclosure 46. Enclosure 46 houses sensor 44 external to airway adapter 38 and may be removed without interrupting the flow of gas. Critical components in enclosure 46 are not exposed to the humidity, blood, mucus, bacteria and viral agents present in the respiratory gas. Airway adapter 38 may be sterilized or discarded between subjects. Laser beam 40 emitted from laser diode 36 is directed through airway adapter 38 which contains respiratory gas 18, onto mirror 48, back through airway adapter 38 onto mirror 50, back through airway adapter 38 onto detector 42. In a preferred embodiment, the pathlength is 66 mm after 3 passes through airway adapter 38. Additional pathlength is obtained, for example, by inserting additional mirrors 48 and 50 into laser beam 40 or by employing other configurations described in the art, such as Herriot cells. Although FIG. 4 shows laser beam 40 passing through respiratory gas three times, a multi-path sensor 44 may be constructed to have any multiple of paths. The advantage of multi-path sensor 44 is increased sensitivity over shorter path length sensors.

Figure 5:
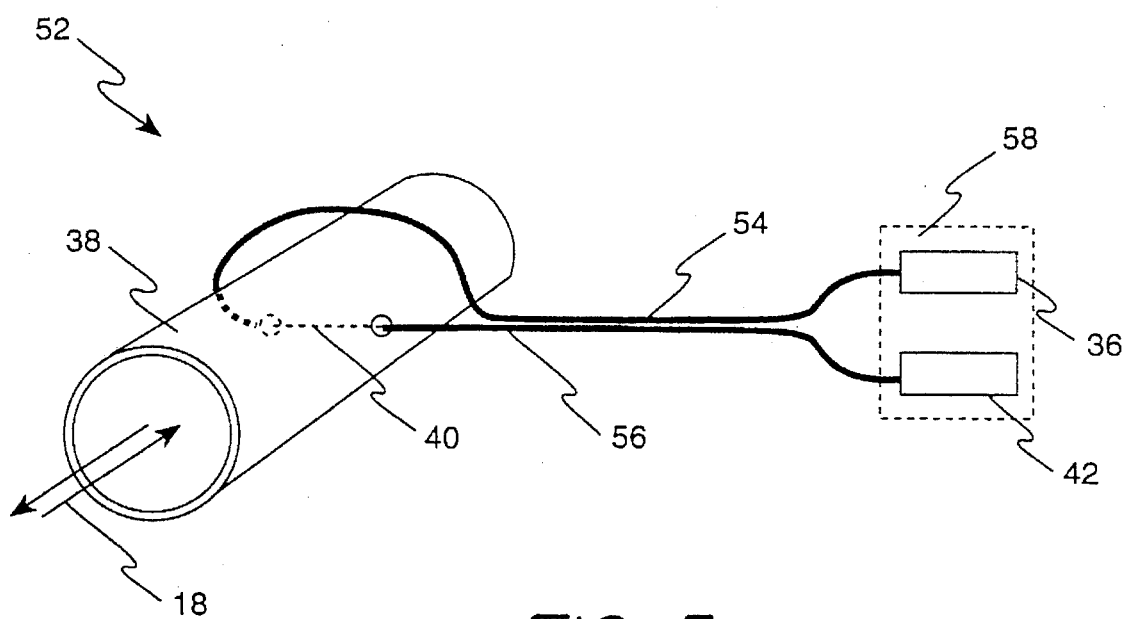
FIG. 5 is a plan view of yet another embodiment of the invention which illustrates a sensor having a laser diode disposed at a remote location from a subject.

Referring now to FIG. 5 there is shown optical fiber coupled sensor 52. Laser diode 36 is coupled to outgoing optical fiber 54 from which laser beam 40 is emitted. Laser beam 40 is directed through airway adapter 38, respiratory gas 18, and into return optical fiber 56, which is coupled to detector 42. Advantages of this embodiment are reduced weight and increased reliability because active components are enclosed in a remote enclosure 58 which is remote from subject 12. It should be appreciated that remote enclosure 58 may be housed in control box 34 of FIG. 3.

Figure 6:
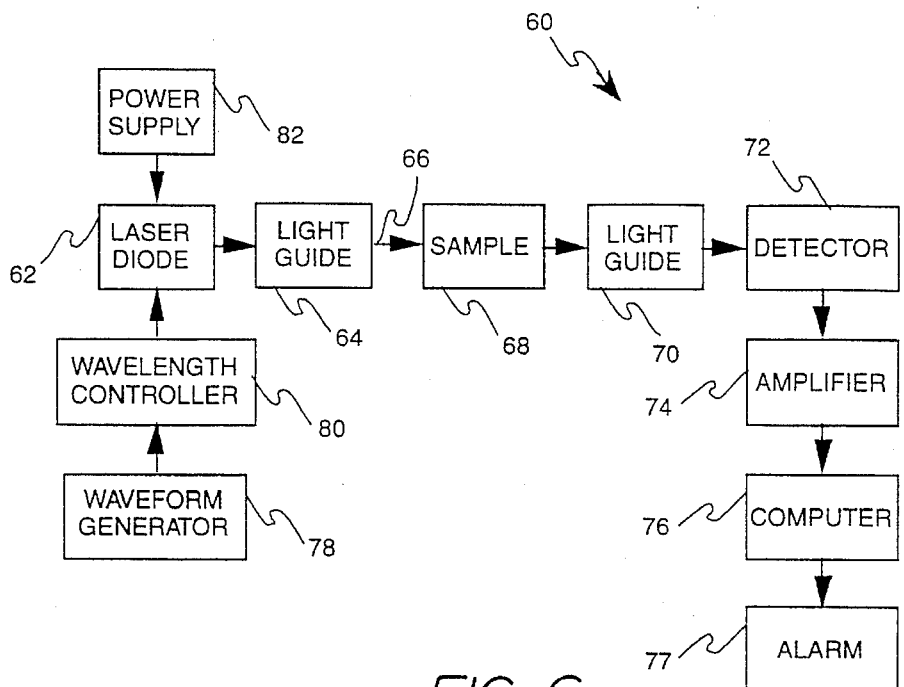
FIG. 6 is a block diagram of the components of a preferred a system utilizing the oxygen sensor constructed in accordance with a preferred embodiment of the invention.

Referring now to FIG. 6, there is shown a block diagram of a sensor system 60. Laser diode 36 is attached to light guide 64 which passes laser beam 66 into sample 68 which contains the molecular species of interest, for example, respiratory oxygen. It should be appreciated that the sample may also be in any state, i.e., a liquid, solid or gas. Laser beam 66 is directed through sample 68, and into light guide 70 which passes the light not absorbed by the molecular species of interest to detector 72. The light transmitted, T, through any uniformly absorbing species is given by the well-known formula:

$$T=e^{-\alpha L}$$

where $\alpha$ is the absorptivity of the species and L is the propagation length. When the product $\alpha L$ is small, the approximation $T=1-\alpha L$ is valid. This results in a variation of detector response which is linear with respect to absorptivity. For most cases of interest, the absorptivity is proportional to the concentration of the molecular species of interest. The detector output is amplified by amplifier 74 to a level suitable for display or analog to digital conversion by an optional computer 76. It should be appreciated that computer 76 may be used to interpret signals from amplifier 74. In a preferred embodiment, computer 76 performs this interpretation at least 20 times per minute in order to continuously sense changes in oxygen consumption. Failure to generate a signal larger than a preset low threshold indicates occlusion of the optical path and an alarm may be annunciated by an optional alarm 77 to indicate sensor 60 has been compromised. This is important in the on-airway oxygen sensor of FIGS. 3B, 4, and 5 because saliva, blood, mucus or condensed water may occlude the optical path which would cause high light absorption and indicate high levels of oxygen when in fact there is none. The slope and frequency of waveform generator 78 are applied to wavelength controller 80 which may be a resistor, thermoelectric cooler or any other device known in the waveform controlling art. Wavelength controller 80 causes the laser beam wavelength to vary through an absorption resonance of the molecular species of interest. Power supply 82 drives laser diode 62 with appropriate characteristics which may include radio frequency modulation for implementation of wavelength or frequency modulated spectroscopy or dual frequency modulation spectroscopy. In this embodiment, laser beam 66, has a wavelength of less than 1.2 micrometers which is continuously tunable and has a frequency linewidth of less than 3 gigahertz.

Figure 7:
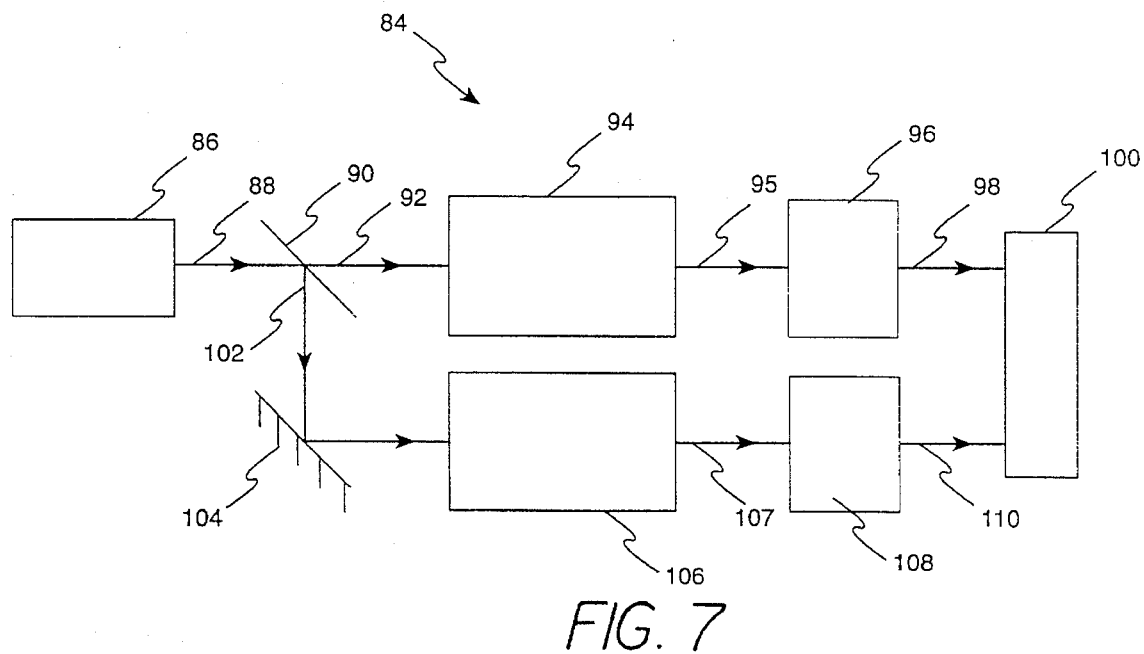
FIG. 7 is a block diagram of an alternate embodiment of the system utilizing an oxygen sensor in which a two path/two detector reference channel is utilized.

Referring now to FIG. 7 there is shown a dual path with dual detector sensor system 84. laser diode 86 emits a beam 88 which is split by beamsplitter 90 into a transmitted beam 92 and a reflected beam 102. Transmitted beam 92 is directed through sample chamber 94 which contains an unknown quantity of the molecular species of interest. The amount of sample light 95 which transmits through sample chamber 94 is measured by detector 96 which sends sample output 98 into processor 100. Reflected beam 102 is reflected by mirror 104 into calibration sample chamber 106 which contains a known amount of the molecular species of interest. The amount of calibration light 107 which transmits through calibration chamber 106 is measured by detector 108 which sends calibration output 110 into processor 100. In cases where the amount of light absorbed by the molecular species in both chambers is small, the amount of unknown molecular species of interest in sample chamber 94 may be approximately equal to sample output 98 divided by calibration output 110 multiplied by the known amount of molecular species of interest in calibration chamber 106. The advantage of dual path with dual detector sensor 84 is that the amount of light absorbed by a known quantity of the molecular species of interest serves to calibrate sensor system 84. It is also possible to direct both sample light 95 and calibration light 107 onto a single detector 96 or 108. In this case it is advantageous to have some means, for example, mechanical or electro-optical (not shown), to insure that only one beam 95 or 107 is incident on the single detector at any given time.

Figure 8A:
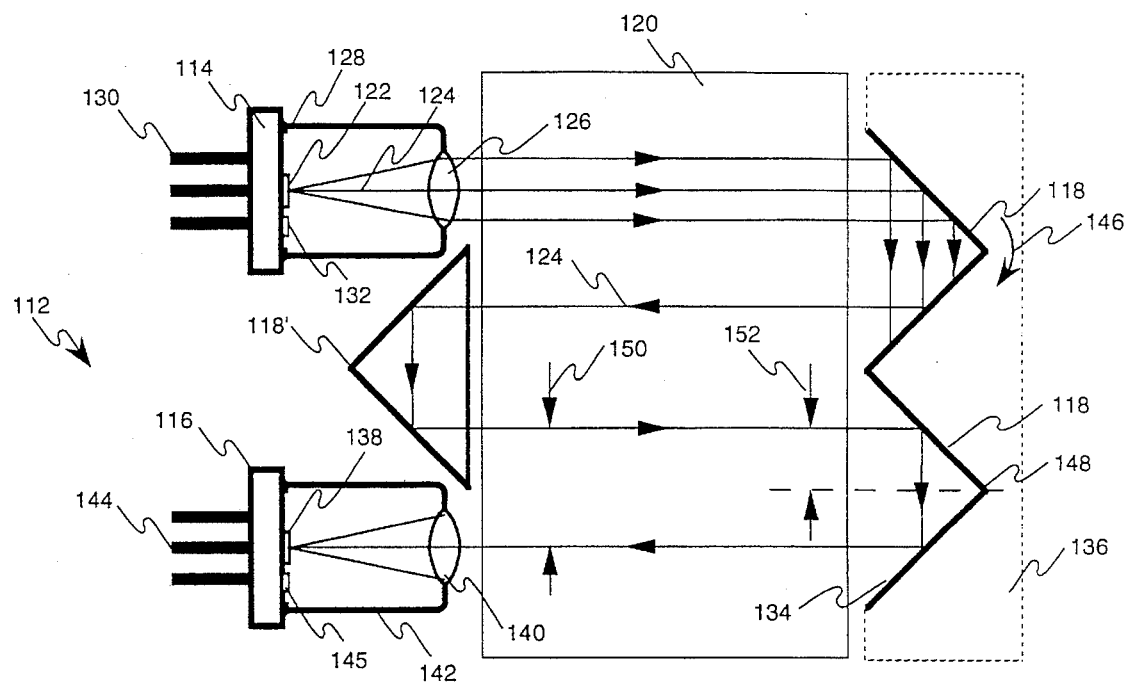
FIG. 8A is a block diagram of an alternate embodiment of the system utilizing an oxygen sensor having multiple paths with a discrete VCSEL and detector.

Referring now to FIG. 8A, there is shown multi-path sensor 112 chiefly comprising laser package 114, detector package 116, retroreflectors 118 and sample chamber 120. Laser package typically comprises laser 122 which emits beam 124, collimating lens 126 which nominally collimates beam 124 and is held in place by housing 128, and electrical contact pins 130. Laser power supply 132 may reside with laser 122 in laser package 114. In the illustration of beam 124, three rays are shown at first to show the collimating of beam 124 by lens 126, however after the reflection from the first retroreflector 118, only the central ray is shown in order to better illustrate the path of beam 124. It should be appreciated that any number of rays in beam 124 may be utilized and those utilized in FIG. 8A are merely representative. Multiple retroreflectors 118 may be formed together in an integrated fashion as seen in retroreflectors 118. Furthermore retroreflectors 118 may utilize external reflection provided, for example, by metallic coatings 134, and be supported by medium 136. Medium 136 may comprise, for example, molded plastic which is rugged, low in cost and light in weight. Alternatively, retroreflectors 118 may utilize internal reflections as shown in retroreflector 118'. Retroreflector 118' may also comprise molded plastic or glass, and may also comprise multiple retroreflectors 118' in a single integrated unit. Any combination of internal or external reflections from retroreflectors 118 or 118' may be employed. Detector package 116 is typically similar in form to laser package 114 and typically comprises detector 138, lens 140 which is held by housing 142, and electrical contact pins 144 providing electrical connection. Amplifying or other electronics 145 may reside with detector 138 in detector package 116. As illustrated in FIG. 8A, beam 124 makes four passes through sample chamber 120, however it is possible for beam 124 to make any number of passes through sample chamber 120. Although not shown, it is possible for laser package 114, detector package 116 and retroreflectors 118 or any combination thereof to be commonly mounted as a single unit.

The use of retroreflectors is advantageous to using conventional mirrors because the angle of propagation of beam 124, after reflection from retroreflector 118, is insensitive to the angular orientation 146 of retroreflector 118, as is well known in the art. Stated differently, beam 124 reflected from retroreflector 118 or 118' propagates parallel to the incident beam, but in the opposite direction. This property depends on retroreflector 118, 118' having a vertex 148 whose angle is exactly 90 degrees. If the angle differs slightly from 90 degrees, the incident and reflected beam directions will differ slightly from being parallel, and will still be fairly insensitive to angular orientation 146. The lateral displacement 150 of beam 124 after reflection from retroreflector 118. 118' is two times the lateral displacement 152 of beam 124 from retroreflector vertex 148. Retroreflectors 118, 118' may be two-dimensional, as depicted in FIG. 8A, in which case they may be visualized as an edge portion of a box. Retroreflectors 118, 118' alternatively, may be three-dimensional, in which case they may be visualized as a corner portion of a cube, and are often referred to as "corner cubes."

Figure 8B:
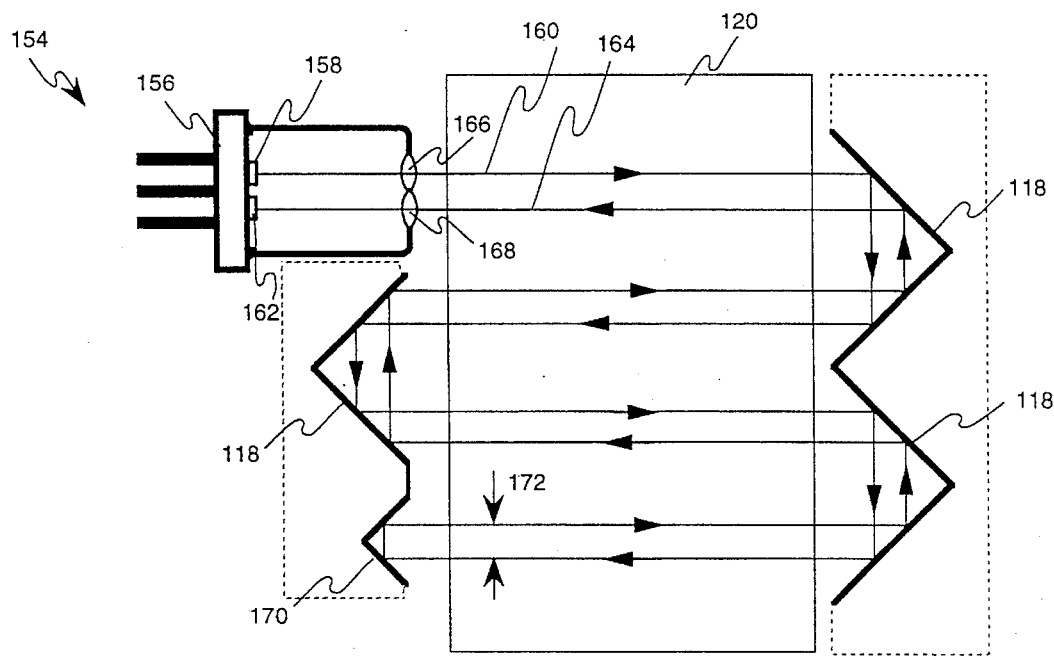
FIG. 8B is a block diagram of an alternate embodiment of the system utilizing an oxygen sensor having multiple paths with VCSEL and detector in the same package.

Referring now to FIG. 8B, there is shown alternative multi-path sensor 154 which also employs retroreflectors 118 or alternatively retroreflectors 118' and sample chamber 120. Package 156 houses both laser 158 which emits outgoing beam 160, and detector 162 which receives incoming beam 164. Preferably, package 156 houses two lenses 166 and 168 for outgoing beam 160 and incoming beam 164, respectively. Outgoing beam 160 is reflected back and forth through sample chamber 120 in a similar manner as was beam 124 of FIG. 8A. In multi-path sensor 154, however, retroreflector 170 produces lateral displacement 172 such that incoming beam 164 is directed through lens 168 which focuses incoming beam 164 onto detector 162. Retroreflectors 118, 118' and 170 may be fabricated as a single piece as previously described. Advantages of multi-path sensor 154, compared to multi-path sensor 112 are that multi-path sensor 154 has only one opto-electronic package, and it achieves twice as many path crossings of sample chamber 120. Package 156 may also contain driver, amplifying or other electronic circuitry (not shown). Although package 156 is shown with two lenses 166 and 168, it is also possible for package 156 to perform the same function with a single lens. In this case, at least one of retroreflectors 118 or 170 should have a vertex angle which differs slightly from 90 degrees, in order for incoming beam 164 to be focused on detector 162 rather than laser 158. Either of the configurations of FIG. 8A or FIG. 8B may be accomplished using any combination of retroreflectors, mirrors, gratings, or refractive elements. It should be appreciated that the preferred embodiment uses retroreflectors.

Figure 9:
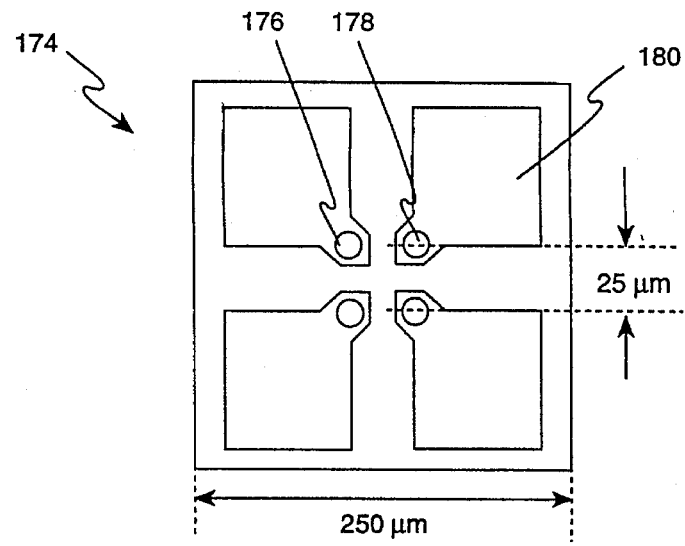
FIG. 9 is a plan view which illustrates an array of lasers on a single chip.

Referring now to FIG. 9, there is shown chip 174 containing a plurality of lasers. Laser 176 and laser 178 each act independently and may emit light at substantially the same wavelength or at substantially different wavelengths. Each laser has a separate electrical bonding pad for making electrical contact. Those familiar in the VCSEL technology will recognize that it is possible to fabricate VCSELs to emit either uniform wavelengths or different wavelengths on a single chip 174, depending on the fabrication process. Similarly, though by using different techniques, it is possible to fabricate distributed feedback (DFB) lasers to emit either uniform wavelengths or different wavelengths on a single chip 174, depending on the fabrication process. When lasers 176 and 178 have nominally the same wavelength, one laser, for example laser 178, may be used to back up the other laser, for example laser 176, in case of failure of laser 178. When lasers 176 and 178 have substantially different emission wavelengths, a choice may be made to use only the laser whose emission wavelength is closest to the desired wavelength, e.g., the wavelength closest to the strongest oxygen absorption resonance.

Figure 1:
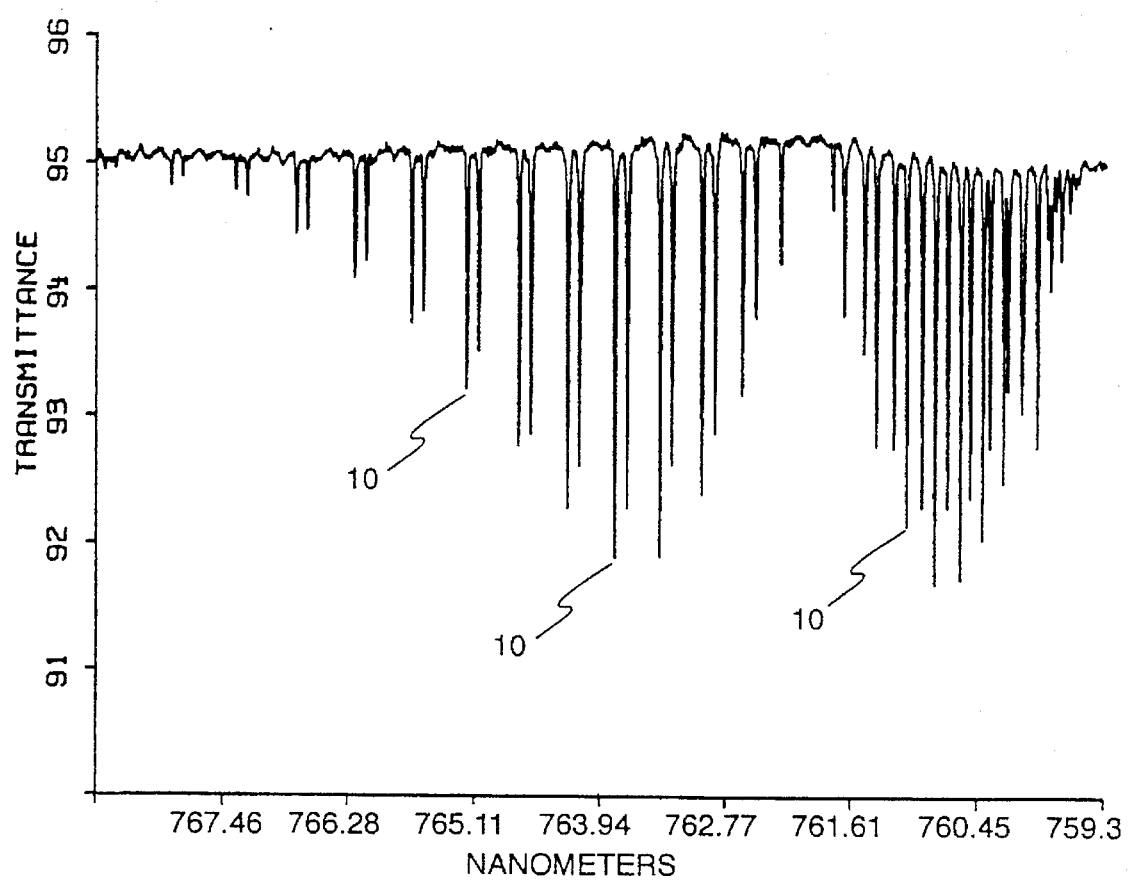
FIG. 1 is a prior art graph of absorption spectrum of oxygen in the 760 nm wavelength region.

Oxygen resonances 10, occurring at wavelengths between 760–764 nm are shown in FIG. 1, see Rothman et at., "The HITRAN database: 1986 edition," *Applied Optics,* 26 (1987). As seen in FIG. 1, the oxygen absorption in the 760 nm region occurs over about a 5 nm width. Since the variation of laser wavelength over a water is usually much larger than 5 nm, much of the wafer might be wasted if each chip 174 contained only a single laser. Having lasers 176 and 178 of different emission wavelengths increases the chances that at least one laser will have an acceptable emission wavelength, and therefore increases the yield of chips 174. The chip dimensions and separations between lasers may be quite small, and may even be smaller than the dimensions shown in FIG. 9. Therefore, in a preferred embodiment, at least one laser 176, 178 will be tuned to approximately 761 nm.

Figure 2:
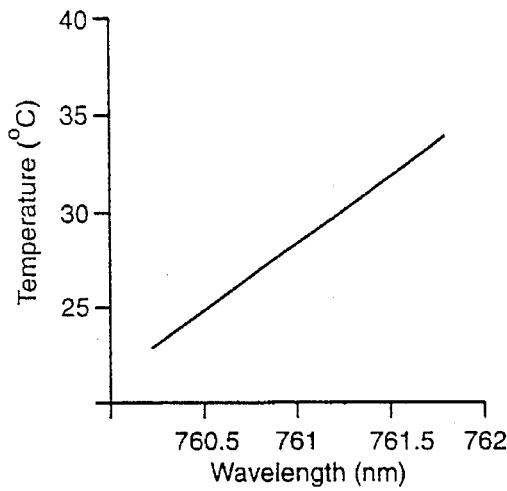
FIG. 2 is a ,graph of wavelength versus temperature for VCSELs.

Olbright, an inventor in this application, showed that VCSELs have a single-cavity resonance with 65-MHz linewidth. See Olbright et al., "Linewidth, Tunability, and VHF Millimeter Wave Frequency Synthesis of Vertical-Cavity GaAs Quantum-Well Surface-Emitting Laser Diode Arrays," *IEEE Photon Tech Lett.,* Vol. 3, No. 779 (1991). The VCSEL's narrow linewidth is much smaller than the 1-GHz wide oxygen absorption linewidth. The emitted wavelength of VCSELs are adjusted to the absorption resonance of oxygen or a molecular species of interest's resonance by varying the temperature of the laser diode as shown in FIG. 2.

Unlike VCSELs, edge-emitting semiconductor laser diodes emitting at wavelengths shorter than 1200 nm exhibit discrete "hops" in wavelength as the temperature or current is varied, and therefore are not continuously tunable. When the VCSEL is tuned to the absorption resonance of a molecular species such as oxygen, light is absorbed, which changes the voltage output of a photodetector which receives light transmitted through the sample. In cases where the amount of light absorbed by the molecular species is small, the voltage change is approximately proportional to the concentration of the molecular species of interest. When the laser wavelength is detuned from the absorption resonance of the molecular species the voltage output of the photodetector is proportional the light loss due to everything except the absorption of the molecular species of interest. This non-resonance voltage serves as a reference to detect changes in light path absorbency caused by condensation, mucus or blood.

Figure 10A:
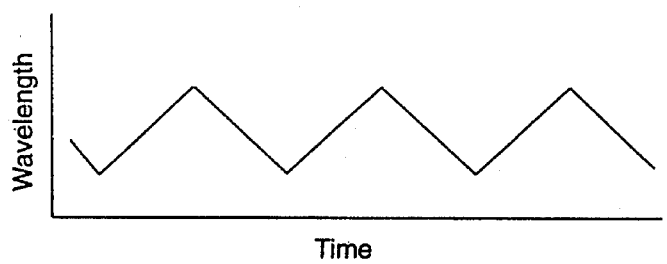
FIG. 10A is a graph of a prior art signal vs. time chart, i.e., a wavelength tuning profile.
Figure 10B:
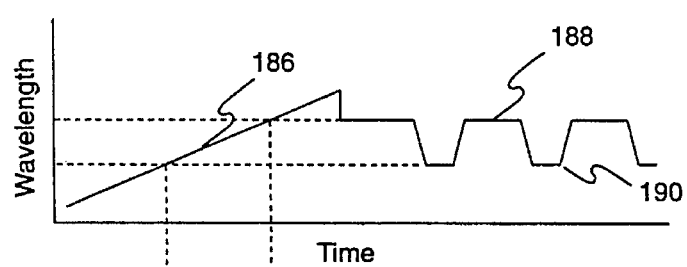
FIG. 10B is a graph of a preferred signal vs. time chart, i.e., a preferred wavelength tuning profile.
Figure 10C:
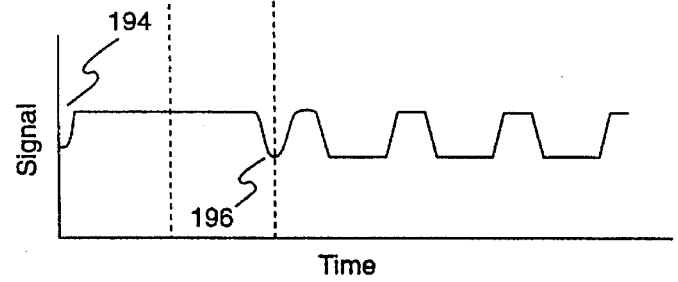
FIG. 10C is a graph of light passing through a sample vs. time for the preferred wavelength tuning profile of FIG. 10B.

Referring now to FIGS. 10A, 10B and 10C, there are shown wavelength vs. time plots for the laser in any of the previously described embodiments of the inventive sensor. FIG. 10A or plot 182 represents a conventional tuning profile in which the laser wavelength is linearly ramped up and down with sufficient range to scan through an absorption resonance. An absorption resonance resembles one of the "spikes" shown in FIG. 1. However, the most useful data is taken when the wavelength is tuned to the maximum absorption of the monitored species. Secondarily useful data is obtained when the absorption of the monitored species is nominally zero. FIG. 10B or plot 184 illustrates a more optimized tuning profile. Initially a broad scan 186 is performed which scans through one or more absorption resonances. Electronic control circuits 34, illustrated in FIG. 3, correlate maximum and minimum absorption of the laser beam with the tuning signals applied to the laser which produced the maximum and minimum absorption's. The tuning means for the laser are then directed to tune the laser such that it spends most of the time at a wavelength 188 corresponding to maximum species absorption, a lesser time at a wavelength 190 corresponding to nominally zero species absorption, and a minimum time at intermediate wavelengths. Broad scan 186 may be repeated as necessary to recalibrate the tuning means. Overall, the signal to noise ratio of the sensor will be enhanced by using a tuning sequence similar to the one illustrated in FIG. 10B. The signal vs. time corresponding to plot 184 is shown in FIG. 10C or plot 192, in which the light signal passing through the sample is plotted vs. time. During broad scan 186, two absorption resonances 194 and 196 are detected which correspond, for example, to two of the absorption resonances seen in FIG. 1. Electronic control circuits 34 choose absorption resonance 196 as having higher strength, and therefore choose the wavelength 188, illustrated in FIG. 10B, for monitoring the absorptive species and wavelength 190 for monitoring the system transmission in the absence (or minimum) of absorption from the absorptive species. Other and similar methods may be used for tuning the wavelength to an absorption resonance such as using the third harmonic signal from a lock-in amplifier as described by Goldstein et al. in "Measurement of molecular concentrations and line parameters using line-locked second harmonic spectroscopy with an AlGaAs diode laser," published in *Applied Optics*, Volume 31, No. 18, pp. 3409–3415 (1992). In that publication, Goldstein et al. also describe the use of second harmonic signals from a lock-in amplifier to produce a derivative-type spectrum, which could also be employed in the operation of the inventive sensor.

It should be appreciated that continuously tunable laser diodes emitting at greater than 1200 nm are known as distributed feedback (DFB) lasers. If in the future it is possible to produce DFB lasers at shorter wavelengths, these short-wavelength DFB lasers may be employed in the invention described above. Finally, it should be appreciated that the above described sensor may be used to detecting any respiratory gas, including but not limited to carbon dioxide. Therefore, metabolic rate monitoring may be accomplished by monitoring both carbon dioxide and oxygen concentrations.

Although the present invention has been fully described in connection with the preferred embodiment thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed is:

1. A respiratory oxygen sensor comprising:
    a first laser diode emitting a first light beam having a first emission wavelength;
    tuning means for tuning said first emission wavelength to an absorption resonance of oxygen;
    means for providing a first respiratory gas sample;
    first directing means for irradiating said respiratory gas sample with said light beam;
    a first detector which receives at least a portion of said light beam and emits signals in response thereto; and
    means for interpreting said signals to measure the concentration of oxygen in said respiratory gas sample.

2. The sensor recited in claim 1 wherein said first laser diode is continuously tunable.

3. The sensor recited in claim 1 wherein said first laser diode is a vertical-cavity surface-emitting laser.

4. The sensor recited in claim 1, further comprising an enclosure in which said first laser diode, said tuning means and said detector are enclosed.

5. The sensor recited in claim 4 wherein said enclosure is coupled to said means for providing a first respiratory gas sample.

6. The sensor recited in claim 5 wherein said first directing means is operable to direct said light beam across said subject's airway tube.

7. The sensor recited in claim 5, further comprising reflectors optically disposed to receive said first light beam, the reflectors being operable to direct said first light beam across said subject's airway tube multiple times.

8. The sensor in claim 7 wherein said reflectors are retroreflectors.

9. The sensor recited in claim 1 wherein said first laser diode and said first detector are held remotely from a subject's airway tube; said sensor further comprising second directing means for directing light from said respiratory gas sample to said first detector.

10. The sensor recited in claim 1 in which said means for interpreting said signals is operable to interpret said signals at a rate of at least 20 times per minute.

11. The sensor recited in claim 1, further comprising a transmission calibrator operable to detect one or more occlusions of said first light beam, said occlusions having one or more causes other than absorption by said oxygen.

12. The sensor recited in claim 11, in which said first detector further comprises an alarm connected to said transmission calibrator, the alarm being operable to emit a signal when said occlusions exceed a predetermined level.

13. The sensor recited in claim 1, further comprising:
    a carbon dioxide monitor operable to measure a carbon dioxide concentration in said first respiratory gas sample, said carbon dioxide monitor being operably coupled to said means for providing a first respiratory gas sample; and
    means for processing information of oxygen concentration and carbon dioxide concentration in order to perform metabolic rate monitoring, said means for processing information being operably coupled to said carbon dioxide monitor.

14. The sensor recited in claim 1 wherein said first emission wavelength is approximately 761 nm.

15. The sensor recited in claim 1, in which said sensor further comprises at least a second laser diode operable to emit a second light beam having a second emission wavelength nominally equal to said first emission wavelength, said second laser diode being operable to emit said second light beam in a direction substantially parallel to the direction of said first light beam.

16. The sensor recited in claim 1, in which said sensor further comprises at least a second laser diode operable to emit a second light beam having a second emission wavelength different from said first emission wavelength, said second laser diode being operable to emit said second light beam in a direction substantially parallel to the direction of said first light beam.

17. The sensor recited in claim 1 wherein said tuning means are operable to control said first emission wavelength to increase the times in which said first emission wavelength is near a maximum of said absorption resonance and essentially off said absorption resonance.

18. An optical sensor comprising:
    at least a first light source, said first light source being continuously tunable and having a frequency linewidth of less than 3 gigahertz, said first light source being operable to emit a first light beam having a first wavelength of less than 1.2 micrometers;
    at least a first power supply for applying power to said first light source;
    first tuning means for tuning said first wavelength;
    means for providing a first sample containing a target species;
    first directing means for irradiating said first sample with said first light beam;
    at least one detector which receives at least a portion of said first light beam and emits signals in response thereto; and means for interpreting said signals.

19. The sensor recited in claim 18 wherein said first light source is a laser.

20. The sensor recited in claim 19 wherein said laser is a vertical-cavity surface-emitting laser.

21. The sensor recited in claim 18 wherein said first light source is contained in a package comprising an integral collimating lens.

22. The sensor recited in claim 18 wherein said first directing means comprises reflectors, said reflectors being operable to produce multiple irradiations through said first sample.

23. The sensor in claim 22 wherein said reflectors are retroreflectors.

24. The sensor recited in claim 18 wherein said tuning means for tuning said wavelength comprises temperature control of said light source.

25. The sensor recited in claim 18 wherein said power applied to said first light source used in conjunction with said means for interpreting said signals comprises wavelength modulation spectroscopy.

26. The sensor recited in claim 18 wherein said power applied to said first light source used in conjunction with said means for interpreting said signals comprises frequency modulation spectroscopy.

27. The sensor recited in claim 18 wherein said power applied to said first light source used in connection with said means for interpreting said signals comprises two tone frequency modulation spectroscopy.

28. The sensor recited in claim 18 wherein said means for interpreting said signals comprises detection of optical absorption of said first light beam.

29. The sensor recited in claim 18, further comprising means for providing a second sample containing a calibration species.

30. The sensor recited in claim 18 wherein said first sample is a respiratory gas.

31. The sensor recited in claim 18 wherein said means for providing a first sample is operable to aspirate said first sample from an external source into a measurement chamber.

32. The sensor recited in claim 18 in which said target species is oxygen.

33. The sensor recited in claim 18, further comprising at least a second light source operable to emit a second light beam having a second emission wavelength nominally equal to said first emission wavelength, said second light source being operable to emit said second light beam in a direction substantially parallel to the direction of said first light beam.

34. The sensor recited in claim 18, further comprising at least a second light source operable to emit a second light beam having a second emission wavelength different from said first emission wavelength, said second light source being operable to emit said second light beam in a direction substantially parallel to the direction of said first light beam.

35. The sensor recited in claim 18 wherein said tuning means is operable to tune said first emission wavelength to increase the times in which said first emission wavelength is near a maximum of said absorption resonance and essentially off said absorption resonance.

36. An optical sensor for determining oxygen concentration in a sample of respiratory air from a subject, said sensor comprising:

a sampler adapted to be mounted on the subject's airway, said sampler having a chamber in which to receive the sample of respiratory air;

a radiation source which comprises a vertical-cavity surface-emitting laser (VCSEL) operable to emit a quantity of radiation, said radiation being optically directed toward said sample of respiratory air; and a detector optically disposed to receive said radiation after said radiation passes through the sample of respiratory air, said detector being operable to generate an output signal corresponding to the concentration of oxygen in the sample of respiratory air based on the intensity of the radiation received by said detector.

37. The sensor recited in claim 36 wherein said sampler is an endotracheal tube.

38. The sensor recited in claim 36 wherein said VCSEL is operable to emit said radiation at a plurality of emission wavelengths.

39. The sensor recited in claim 38 wherein said VCSEL is operable to emit one or more of said emission wavelengths based upon the temperature of said VCSEL.

40. The sensor recited in claim 36 further comprising a means for providing a second sample of gas containing a known concentration of oxygen.

41. The sensor recited in claim 36 wherein the sensor weighs less than 50 grams.

42. The sensor recited in claim 36 wherein the sensor weighs less than 30 grams.

43. The sensor recited in claim 36, further comprising reflectors optically disposed to receive said radiation, the reflectors being operable to direct said radiation across the sample of respiratory air multiple times.

44. The sensor recited in claim 43, wherein said reflectors are retroreflectors.

45. An optical sensor for determining oxygen concentration in a sample of respiratory air from a subject, said sensor comprising:

a sampler adapted to be mounted on the subject's airway, said sampler having a chamber in which to receive the sample of respiratory air;

a radiation source comprising a laser diode operable to emit a quantity of radiation, said radiation being optically directed toward the sample of respiratory air;

a detector optically disposed to receive said radiation after said radiation passes through the sample of respiratory air, said detector being operable to generate an output signal corresponding to the concentration of oxygen in the sample of respiratory air based on the intensity of said radiation received by said detector; and wherein said laser diode is not coupled to a heat sink.

46. An optical sensor for determining oxygen concentration in a sample of respiratory air from a subject, said sensor comprising:

a sampler adapted to be mounted on the subject's airway, said sampler having a chamber in which to receive the sample of respiratory air;

a radiation source operable to emit a quantity of radiation, said radiation being optically directed toward the sample of respiratory air;

a detector optically disposed to receive said radiation after said radiation passes through the sample of respiratory air, said detector being operable to generate an output signal corresponding to the concentration of oxygen in the sample of respiratory air based on the intensity of the radiation received by said detector; and wherein said radiation source is continuously tunable.

47. The sensor recited in claim 36 or 46, wherein said radiation source is operable to emit said quantity of radiation having an emission wavelength of approximately 760 to 763 nm.

48. An optical sensor for determining oxygen concentration in a sample of respiratory air from a subject, said sensor comprising:

a sampler adapted to be mounted on the subject's airway, said sampler having a chamber in which to receive the sample of respiratory air;

a radiation source operable to emit a quantity of radiation, said radiation being optically directed toward the sample of respiratory air;

a detector optically disposed to receive said radiation after said radiation passes through the sample of respiratory air, said detector being operable to generate an output signal corresponding to the concentration of oxygen in the sample of respiratory air based on the intensity of said radiation received by said detector; and means for interpreting said output signal, said means for interpreting said output signal operable to interpret said output signal at a rate of at least 20 times per minute.

49. The sensor recited in claim 48 wherein said means for interpreting said output signal is operable to measure the difference between the oxygen concentration in said sample of respiratory air, and a second oxygen concentration in a second sample of air.

50. The sensor recited in claim 49 wherein the sample of respiratory air comprises inspired air, and the second sample of air comprises expired air.

51. An optical sensor for determining oxygen concentration in a sample of respiratory air from a subject, said sensor comprising:

a sampler adapted to be mounted on the subject's airway, said sampler having a chamber in which to receive the sample of respiratory air;

a radiation source operable to emit a quantity of radiation, said radiation being optically directed toward the sample of respiratory air;

a detector optically disposed to receive said radiation after said radiation passes through the sample of respiratory air, said detector being operable to generate an output signal corresponding to the concentration of oxygen in the sample of respiratory air based on the intensity of said radiation received by said detector;

means for interpreting said output signal, said interpreting means operable to detect the difference between the oxygen concentration in the sample of respiratory air, and a second oxygen concentration in a second sample of air, the difference being less than 3 volume percent of said oxygen concentrations.

52. An optical sensor for determining oxygen concentration in a sample of respiratory air from a subject, said sensor comprising:

a sampler adapted to be mounted on the subject's airway, said sampler having a chamber in which to receive the sample of respiratory air;

a radiation source operable to emit a quantity of radiation, said radiation being optically directed toward the sample of respiratory air;

a detector optically disposed to receive said radiation after said radiation passes through the sample of respiratory air, said detector being operable to generate an output signal corresponding to the concentration of oxygen in the sample of respiratory air based on the intensity of said radiation received by said detector;

means for interpreting said output signal, said interpreting means operable to detect the difference between the oxygen concentration in the sample of respiratory air, and a second oxygen concentration in a second sample of air, said difference being less than 0.5 volume percent of said oxygen concentrations.

53. An optical sensor for determining oxygen concentration in a sample of respiratory air from a subject, said sensor comprising:

a sampler adapted to be mounted on the subject's airway, said sampler having a chamber in which to receive the sample of respiratory air;

a radiation source operable to emit a quantity of radiation, said radiation being optically directed toward the sample of respiratory air;

a detector optically disposed to receive said radiation after said radiation passes through the sample of respiratory air, said detector being operable to generate an output signal corresponding to the concentration of oxygen in the sample of respiratory air based on the intensity of said radiation received by said detector; wherein the sensor is operable to have a response time of less than 15 seconds.

54. An optical sensor for determining oxygen concentration in a sample of respiratory air from a subject, said sensor comprising:

a sampler adapted to be mounted on the subject's airway, said sampler having a chamber in which to receive the sample of respiratory air;

a radiation source operable to emit a quantity of radiation, said radiation being optically directed toward the sample of respiratory air;

a detector optically disposed to receive said radiation after said radiation passes through the sample of respiratory air, said detector being operable to generate an output signal corresponding to the concentration of oxygen in the sample of respiratory air based on the intensity of said radiation received by said detector; wherein the sensor is operable to have a response time of less than 1 second.

55. An optical sensor for determining oxygen concentration in a sample of respiratory air from a subject, said sensor comprising:

a sampler adapted to be mounted on the subject's airway, said sampler having a chamber in which to receive the sample of respiratory air;

a radiation source operable to emit a quantity of radiation, said radiation being optically directed toward the sample of respiratory air;

a detector optically disposed to receive said radiation after said radiation passes through the sample of respiratory air, said detector being operable to generate an output signal corresponding to the concentration of oxygen in the sample of respiratory air based on the intensity of said radiation received by said detector; and a transmission calibrator operable to detect one or more occlusions of said radiation, said occlusions having one or more causes other than absorption by said oxygen.

56. An optical sensor for determining oxygen concentration in a sample of respiratory air from a subject, said sensor comprising:

a sampler adapted to be mounted on the subject's airway, said sampler having a chamber in which to receive the sample of air;

a radiation source operable to emit a quantity of radiation, said radiation having an emission wavelength and being optically directed toward the sample of respiratory air;

a detector optically disposed to receive said radiation after said radiation passes through the sample of respiratory air, said detector being operable to generate an output signal corresponding to the concentration of oxygen in the sample of respiratory air based on the intensity of said radiation received by said detector; and at least a second radiation source, said second radiation source being operable to emit a second quantity of radiation with a second emission wavelength approximately equal to the emission wavelength of said quantity of radiation, and said second quantity of radiation being optically directed toward the sample of respiratory air.

57. An optical sensor for determining oxygen concentration in a sample of respiratory air from a subject, said sensor comprising:

a sampler adapted to be mounted on the subject's airway, said sampler having a chamber in which to receive the sample of respiratory air;

a radiation source operable to emit a quantity of radiation, said radiation having an emission wavelength and being optically directed toward the sample of respiratory air;

a detector optically disposed to receive said radiation after said radiation passes through the sample of respiratory air, said detector being operable to generate an output signal corresponding to the concentration of oxygen in the sample of respiratory air based on the intensity of said radiation received by said detector; and at least a second radiation source, said second radiation source being operable to emit a second quantity of radiation with a second emission wavelength different from the emission wavelength of said quantity of radiation, and said second quantity of radiation being optically directed toward the sample of respiratory air.

58. The sensor recited in claim 45, 46, 48, 51, 52, 53, 54, 55, 56 or 57 wherein said radiation source is a VCSEL.

59. An optical sensor for determining a gaseous component's concentration in a sample of air from a subject, said sensor comprising:

a sampler having a chamber in which to receive the sample of air;

a vertical-cavity surface-emitting laser operable to emit a quantity of radiation, said radiation being optically directed toward the sample of air;

a detector optically disposed to receive said radiation after the radiation passes through the sample of air, the detector being operable to generate an output signal corresponding to the concentration of said gaseous component in the sample of air based on the intensity of the radiation received by the detector.

60. A method for determining a gaseous component's concentration in a sample of air from a subject, said method comprising the steps of:

collecting the sample of air;

emitting a quantity of radiation optically directed toward the sample of air, wherein said step of emitting is performed using a vertical-cavity surface-emitting laser;

receiving the radiation in a detector, after the radiation passes through the sample of air;

generating an output signal, using the detector, corresponding to the concentration of said gaseous component in the sample of air based on the intensity of the radiation received by the detector.

* * * * *